US011149055B2

(12) United States Patent
Liu et al.

(10) Patent No.: US 11,149,055 B2
(45) Date of Patent: Oct. 19, 2021

(54) CRYSTAL FORM OF LANOSTEROL PRODRUG COMPOUND AND APPLICATION THEREOF

(71) Applicant: GUANGZHOU OCUSUN OPHTHALMIC BIOTECHNOLOGY CO., LTD., Guangdong (CN)

(72) Inventors: Yizhi Liu, Guangdong (CN); Yandong Wang, Guangdong (CN); Xiaolin Li, Shanghai (CN); Zhi Luo, Shanghai (CN); Haiying He, Shanghai (CN); Jian Li, Shanghai (CN); Shuhui Chen, Shanghai (CN)

(73) Assignee: GUANGZHOU OCUSUN OPHTHALMIC BIOTECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 17/262,483

(22) PCT Filed: Jul. 25, 2019

(86) PCT No.: PCT/CN2019/097773
§ 371 (c)(1),
(2) Date: Jan. 22, 2021

(87) PCT Pub. No.: WO2020/020306
PCT Pub. Date: Jan. 30, 2020

(65) Prior Publication Data
US 2021/0246158 A1    Aug. 12, 2021

(30) Foreign Application Priority Data
Jul. 25, 2018 (CN) .......................... 201810826425.6

(51) Int. Cl.
*C07J 9/00* (2006.01)
(52) U.S. Cl.
CPC ............ *C07J 9/00* (2013.01); *C07B 2200/13* (2013.01)
(58) Field of Classification Search
CPC .......................... C07J 9/00; C07B 2200/13
See application file for complete search history.

(56) References Cited

U.S. PATENT DOCUMENTS

| 4,861,878 A | 8/1989 | Fengler et al. |
| 10,471,076 B2 | 11/2019 | Zhang et al. |
| 10,738,076 B2 | 8/2020 | Liu et al. |
| 2019/0256548 A1* | 8/2019 | Liu .................. A61P 27/12 |

FOREIGN PATENT DOCUMENTS

| CN | 107206009 | 9/2017 |
| CN | 107206009 A | 9/2017 |
| JP | S62120398 A | 6/1987 |
| RU | 2283318 C1 | 9/2006 |
| RU | 2720677 C1 | 5/2020 |
| WO | 2016029197 A1 | 2/2016 |
| WO | 2016029199 A1 | 2/2016 |
| WO | WO-2016/029197 A1 | 2/2016 |
| WO | 2018137683 A1 | 8/2018 |

OTHER PUBLICATIONS

Written Opinion of the International Searching Authority dated Oct. 29, 2019 issued in International Applicaton No. PCT/CN2019/097773, with English translation, 10 pages.
International Search Report dated Oct. 29, 2019 issued in International Application No. PCT/CN2019/097773 with English translation, 6 pages.
Written Opinion of the International Searching Authority dated Oct. 29, 2019 issued in International Application No. PCT/CN2019/097773 with English translation, 10 pages.
Unpublished Chinese Priority Patent Application No. 201810826425.6 filed Jul. 25, 2018, with English translation, 46 pages.
Dikusar, E.A., et al., "Synthesis of Some Terpene-Alcohol, Sterol, and Plant Phenol Esters of 4,5-Dichloroisothiazol-3-Carboxylic Acid," Chemistry of Natural Compounds, vol. 39, No. 2, 2003, 2 pages.
Wieland, von Heinrich, et al., Uber die Nebensterine der Hefe. IV. Kryptosterin, Liebigs Ann. Chem., 1937, vol. 529, pp. 68-83.
Stokes, William M., "The Separation of the Compounds of the Lanosterol Group Present in "Isocholesterol" by Chromatography of the p-Iodobenzoates-I and Benzoates", Archives of Biochemistry and Biophysics, 1957, vol. 67, pp. 272-279.
Gray, Allan P., et al., "Steroid Antifertility Agents. Ionic Complexes of Basic Derivatives for Prolonged Action", Journal of Medicinal Chemistry, 1978, vol. 21, No. 7, pp. 712-715.
Notice of Reason for Refusal dated Jun. 29, 2021 issued in counterpart JP Application No. 2021-509916, with English translation, 5 pages.
Office Action dated Aug. 5, 2021 issued in RU Application No. 2021103501/04, with partial English translation, 15 pages.

\* cited by examiner

*Primary Examiner* — John M Mauro
(74) *Attorney, Agent, or Firm* — Foley & Lardner LLP

(57) ABSTRACT

The present invention relates to a crystal form of a compound of formula (I) and an application thereof in preparing a drug for treating an ophthalmic disease.

8 Claims, 5 Drawing Sheets

CRYSTAL FORM OF LANOSTEROL PRODRUG COMPOUND AND APPLICATION THEREOF

CROSS-REFERENCE TO RELATED APPLICATIONS

The present application is a 371 of PCT/CN2019/097773, filed Jul. 25, 2019, which is based upon and claims priority to Chinese patent application CN201810826425.6, filed on Jul. 25, 2018, both of which are incorporated herein by reference in their entireties.

TECHNICAL FIELD

The present disclosure relates to a crystalline form of the compound of formula (I) and an application thereof in preparing a drug for treating an ophthalmic disease.

BACKGROUND

Cataract is a disease of the eye which occurs in the crystalline lens in the eyeball and the crystalline lens turbidity is collectively called cataract. Aging, heredity, metabolic abnormality, trauma, radiation, poisoning and local malnutrition can cause damage to the crystalline lens capsule resulting in increase of permeability and lose of barrier function, or cause metabolic disorders of the crystalline lens resulting in denaturation of crystalline lens protein and formation of turbidity. If the crystalline lens of the eyeball changes from transparence to opacity and has an impact on the sunlight received by eyes, it will affect the eyesight of the eyes. When the degree of turbidity of eyeball is light, the effect on vision is lighter, but as the degree of turbidity gradually deepens, the visual acuity will increase, and severe cases will lead to blindness. Cataract is one of the most common eye diseases leading to blindness and it is a major cause of blindness. Since the mechanism of cataract formation is still unclear, no breakthrough has been made in drug therapy. Therefore, currently the only effective treatment is surgical treatment.

Although the continuous improvement of cataract surgery has provided great assistance to the treatment of cataract, the cure rate of surgical treatment is still far below the incidence rate, and there is the possibility of serious complications. On the other hand, the cost of surgical treatment of cataract is very high, and even in developed countries, cataract imposes a huge burden on the medical insurance system. Therefore, the prevention and treatment with drugs play a decisive role. At present, therapeutic drugs available clinically for cataract include: 1, aldose reductase inhibitors, such as cataline (Catalin, Kary Uni, Prifenoxinesodium), phacolysin, bendazac L-lysine, etc.; 2, anti-oxidative damage drugs, such as glutathione, taurine, aspirin, etc.; 3, nutrient metabolism drugs, such as vitamins, carotenoids, etc.; 4, Chinese herbal compound including Shihu Yeguang Pill, Qiju Dihuang Pill, Shijueming San and so on. It has been confirmed by long-term clinical trials that these drugs for the treatment of cataract can only delay the deterioration of cataract, but cannot reverse the condition so as to treat cataract. Meanwhile, as China begins to enter an aging society, the number of cataract patients is increasing, and the demand for cataract drugs will become more urgent. Therefore, new varieties of ophthalmic external anti-cataract drugs with safety, good curative effect, strong intraocular penetration and stable nature are needed clinically.

Lanosterol is an amphiphilic molecule enriched in the crystalline lens. It is synthesized from lanosterol synthase (LSS) through a key cyclization reaction of the cholesterol synthesis pathway. Lanosterol can reduce the abnormal aggregation of crystalline lens proteins and make them regularly rearranged to restore crystal transparency. Studies have shown that lanosterol synthase can be detected in the crystalline lens. Furthermore, in the Shumiya cataract rat study, a specific combination of homozygous mutations of lanosterol synthase and farnesyl diphosphate farnesyltransferase 1 (FDFT1) can alleviate cholesterol levels in the crystalline lens and cause cataract. Meanwhile, our recent studies have found that lanosterol can significantly reduce preformed crystalline lens protein aggregates in vitro and at cellular level. It has also been confirmed that lanosterol can reverse the condition of cataract and bring about clarification and transparency of the crystalline lens in vivo. This result has recently been published in Nature and attracted worldwide attention and it is a new molecule for the prevention and treatment of cataract.

Content of the Invention

The present disclosure provides a crystal form A of the compound of formula (I), wherein the X-ray powder diffraction pattern (XPRD) of the crystal form A comprises characteristic diffraction peaks at the following angles of 2θ: 8.60±0.2°, 15.06±0.2° and 17.22±0.2°.

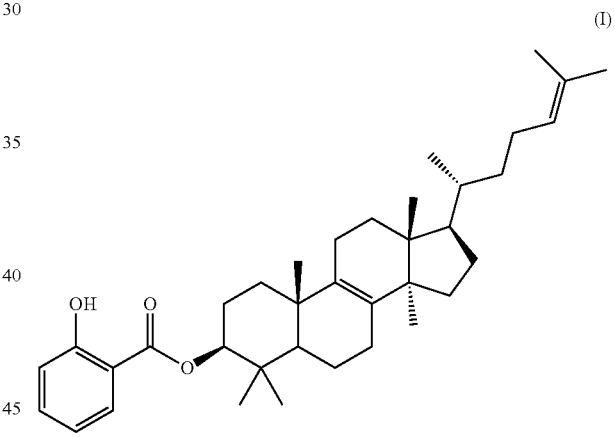

(I)

In some embodiments of the present disclosure, the X-ray powder diffraction pattern of the crystal form A comprises characteristic diffraction peaks at the following angles of 2θ: 8.60±0.2°, 9.38±0.2°, 10.57±0.2°, 12.54±0.2°, 14.43±0.2°, 15.06±0.2°, 17.22±0.2° and 25.18±0.2°.

In some embodiments of the present disclosure, the X-ray powder diffraction pattern of the crystal form A comprises characteristic diffraction peaks at the following angles of 2θ: 4.350°, 8.598°, 9.383°, 10.566°, 12.542°, 13.448°, 14.428°, 14.591°, 15.063°, 15.453°, 15.820°, 16.803°, 17.216°, 20.985°, 21.181°, 22.225°, 22.601°, 22.856°, 23.726°, 24.039°, 24.534°, 25.185°, 25.514°, 25.935°, 26.570°, 27.867°, 28.125°, 28.416°, 29.114°, 29.445°, 31.914°, 33.710°, 34.297°, 34.329°, 36.014°, 36.108° and 38.196°.

In some embodiments of the present disclosure, the X-ray powder diffraction pattern of the crystal form A is as shown in FIG. 1.

In some embodiments of the present disclosure, the analytical data of the X-ray powder diffraction pattern of the crystal form A is as shown in Table 1.

TABLE 1

Analytical data of the XRPD pattern of the crystal form A

| No. | Angle of 2θ(°) | d-spacing (Å) | Relative intensity | No. | Angle of 2θ(°) | d-spacing (Å) | Relative intensity |
|---|---|---|---|---|---|---|---|
| 1 | 4.350 | 20.297 | 20.2 | 20 | 24.039 | 3.6989 | 4.6 |
| 2 | 8.598 | 10.2761 | 85.3 | 21 | 24.534 | 3.6255 | 4.8 |
| 3 | 9.383 | 9.4178 | 6.4 | 22 | 25.185 | 3.5331 | 16.8 |
| 4 | 10.566 | 8.366 | 8.4 | 23 | 25.514 | 3.4884 | 2.4 |
| 5 | 12.542 | 7.0517 | 11.2 | 24 | 25.935 | 3.4327 | 5.4 |
| 6 | 13.448 | 6.5785 | 3.4 | 25 | 26.570 | 3.352 | 4.8 |
| 7 | 14.428 | 6.1338 | 47 | 26 | 27.867 | 3.1989 | 2.9 |
| 8 | 14.591 | 6.0658 | 39.8 | 27 | 28.125 | 3.1701 | 1.7 |
| 9 | 15.063 | 5.8766 | 50.3 | 28 | 28.416 | 3.1384 | 2 |
| 10 | 15.453 | 5.7294 | 5.3 | 29 | 29.114 | 3.0646 | 3.4 |
| 11 | 15.820 | 5.5974 | 14 | 30 | 29.445 | 3.031 | 1.6 |
| 12 | 16.803 | 5.2721 | 78.4 | 31 | 31.914 | 2.8019 | 1.7 |
| 13 | 17.216 | 5.1464 | 100 | 32 | 33.710 | 2.6566 | 3.8 |
| 14 | 20.985 | 4.2298 | 4.7 | 33 | 34.297 | 2.6124 | 3.7 |
| 15 | 21.181 | 4.1912 | 12.5 | 34 | 34.329 | 2.6101 | 2 |
| 16 | 22.225 | 3.9965 | 3 | 35 | 36.014 | 2.4917 | 1.6 |
| 17 | 22.601 | 3.9309 | 3.5 | 36 | 36.108 | 2.4855 | 1.3 |
| 18 | 22.856 | 3.8876 | 2.4 | 37 | 38.196 | 2.3543 | 2.1 |
| 19 | 23.726 | 3.7469 | 4.7 | | | | |

In some embodiments of the present disclosure, the differential scanning calorimetry (DSC) pattern of the crystal form A has an endothermic peak with onset at 151.75±3° C.

In some embodiments of the present disclosure, the DSC pattern of the crystal form A is as shown in FIG. 2.

In some embodiments of the present disclosure, the thermogravimetric analysis (TGA) pattern of the crystal form A has a weight loss of 0.04540% occurred at 151.57±3° C.

In some embodiments of the present disclosure, the TGA pattern of the crystal form A is as shown in FIG. 3.

The present disclosure also provides a use of the crystal form A in the manufacture of a medicament for treating ophthalmic disease.

Technical Effect

As a new prodrug of lanosterol, the compound of the present disclosure has good permeability and is effectively converted into lanosterol in the body, which greatly improves the drug utilization rate of lanosterol; the crystal form thereof has good stability.

Definition and Description

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The solvents used in the present disclosure are commercially available. The present disclosure employs the following abbreviations: DCM represents dichloromethane; DMF represents N,N-dimethylformamide; DMSO represents dimethyl sulfoxide; EtOH represents ethanol; MeOH represents methanol; TFA represents trifluoroacetic acid; TsOH represents p-toluenesulfonic acid; mp represents melting point; EtSO$_3$H represents ethanesulfonic acid; MeSO$_3$H represents methanesulfonic acid; ATP represents adenosine triphosphate; HEPES represents 4-hydroxyethylpiperazine ethanesulfonic acid; EGTA represents ethylene glycol bis(2-aminoethyl ether) tetraacetic acid; MgCl$_2$ represents magnesium dichloride; MnCl$_2$ represents manganese dichloride; DTT represents dithiothreitol; DCC represents dicyclohexylcarbodiimide; DMAP represents 4-dimethylaminopyridine; lanosterol prodrug 026 represents the compound of formula (I) of the present disclosure.

X-ray powder diffractometer, XRPD

About 10 to 20 mg of the sample was subjected to XRPD detection.

Detailed XRPD parameters are as follows:

X-ray tube: Cu, kα, (λ=1.54056Å)

X-ray tube voltage: 40 kV, X-ray tube current: 40 mA

Divergence slit: 0.60 mm

Detector slit: 10.50 mm

Anti-scattering slit: 7.10 mm

Scanning range: 4-40 deg

Step size: 0.02 deg

Step time: 0.12 second

Rotation speed of sample tray: 15 rpm

Dynamic Vapor Sorption (DVS)

Detection method: samples (10 mg to 20 mg) were placed in a DVS sample tray for testing.

Temperature: 25° C.

Equilibrium: dm/dt: 0.01%/min: (Shortest: 10 min, longest: 180 min)

Drying: 0% RH, 120 min

RH (%) gradient for testing: 10%

RH (%) gradient range for testing: 0% to 90% to 0%

The hygroscopicity was evaluated using the following scales:

| Scales for hygroscopicity | Hygroscopic weight gain* |
|---|---|
| Deliquescence | Absorbing sufficient water to form liquid |
| High hygroscopicity | Hygroscopic weight gain ≥ 15% |
| Medium hygroscopicity | 15% > Hygroscopic weight gain ≥ 2% |
| Slight hygroscopicity | 2% > Hygroscopic weight gain ≥ 0.2% |
| No or almost no hygroscopicity | Hygroscopic weight gain ≥ 0.2% |

*Hygroscopic weight gain at 25 ± 1° C. and 80 ± 2% RH

DETAILED DESCRIPTION OF THE EMBODIMENT

For better understanding of the content of the present disclosure, the present disclosure is described in detail through the embodiments, which does not mean any limitation on the present disclosure.

Reference Example 1: Fragment BB-1

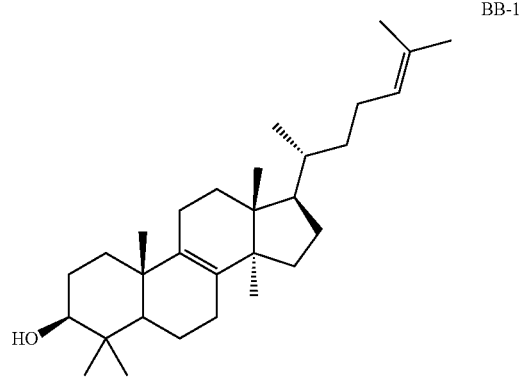 [SMILES: CC(C)=CCC[C@@H](C)[C@H]1CC[C@@]2(C)C3=C(CC[C@]12C)[C@@]1(C)CC[C@H](O)C(C)(C)C1CC3]

Synthetic Route:

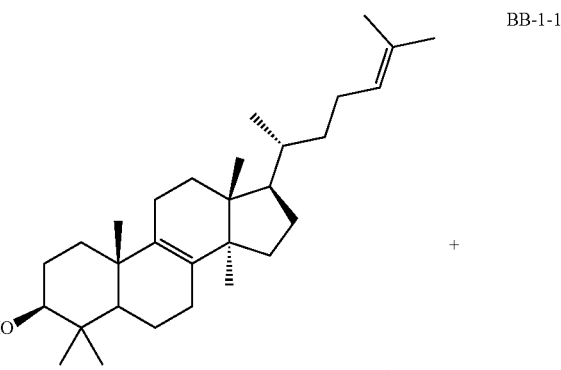

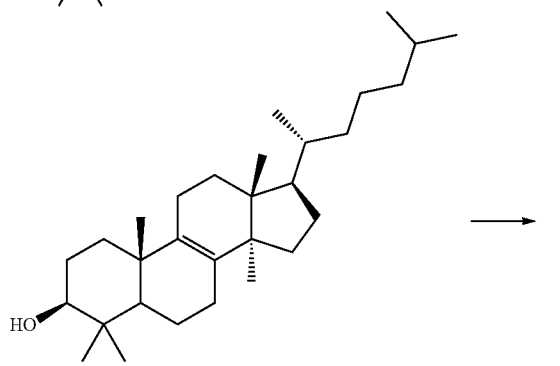

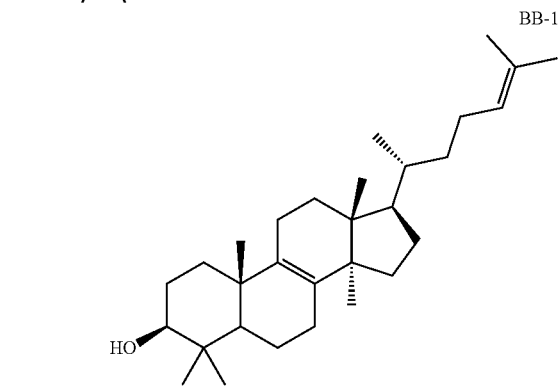

Step 1: Synthesis of compound BB-1.

The mixture BB-1-1 was subjected to supercritical fluid chromatography (Separation conditions: column: Chiralpak AD-3 150×4.6 mm I.D., 3 μm; Mobile phase: A: $CO_2$, B: ethanol (0.05% diethanolamine); gradient: B from 5% to 40% in 5 minutes, B 40% maintained for 2.5 minutes, then B 5% maintained for 2.5 minutes; flow rate: 2.5 mL/min; column temperature: 35° C.; wavelength: 220 nm) to give compound BB-1. $^1$H NMR (CDCl$_3$ 400 MHz): δ=5.06-5.15 (m, 1H), 5.10 (br t, J=7.2 Hz, 1H), 3.20-3.22 (m, 1H), 3.24 (dd, J=11.5, 4.5 Hz, 1H), 1.64-2.09 (m, 15H), 0.77-1.57 (m, 29H), 0.65-0.72 ppm (m, 3H).

Example 1: Preparation of the Compound of Formula (I)

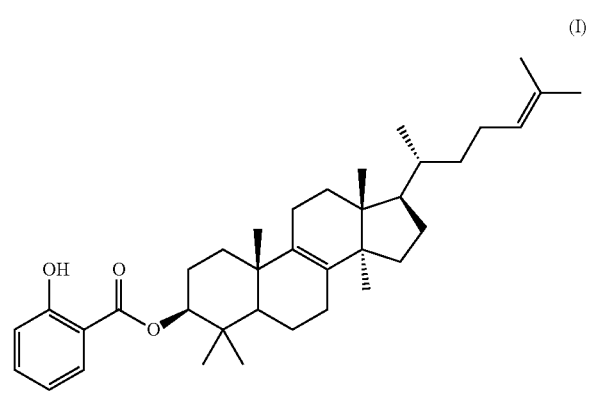 [SMILES: CC(C)=CCC[C@@H](C)[C@H]1CC[C@@]2(C)C3=C(CC[C@]12C)[C@@]1(C)CC[C@H](OC(=O)c2ccccc2O)C(C)(C)C1CC3]

(I)

Synthetic Route:

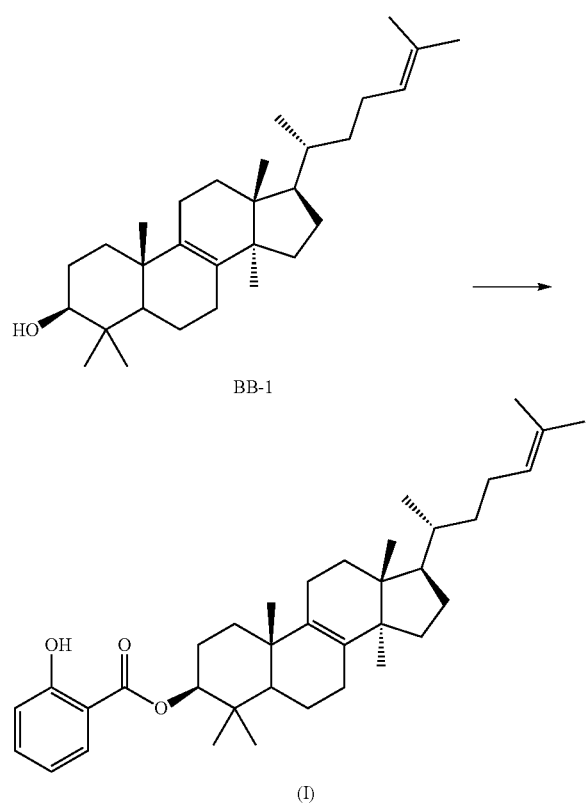

Step 1: Synthesis of the Compound of Formula (I).

35.2 g of compound BB-1 was dissolved in 550 mL of anhydrous dichloromethane, 22.8 g of salicylic acid was added, then 39.2 g of DCC was added, and finally 23.2 g of DMAP was added, resulting in a white suspension, which was heated to 35° C. and the reaction was allowed to run for 96 hours. TLC showed that a small amount of raw materials remained, and the reaction was stopped. The reaction mixture was filtered, the filter residue was washed with 150 mL of dichloromethane, and the filtrate was combined and concentrated to dryness to give a crude residue. 500 mL of methanol was added to the crude residue and refluxed for 16 hours to give a white suspension, the temperature was lowered to 15° C., and the mixture was filtered to give a white solid, which was confirmed as the crystal form A of the compound of formula (I) after XRPD testing.

$^1$H NMR (400 MHz, CDCl$_3$) δ 10.89 (s, 1H), 7.77 (dd, J=1.76, 8.03 Hz, 1H), 7.38 (ddd, J=1.76, 7.09, 8.47 Hz, 1H), 6.91 (dd, J=0.88, 8.41 Hz, 1H), 6.78-6.85 (m, 1H), 5.00-5.07 (m, 1H), 4.68-4.74 (m, 1H), 1.64-2.04 (m, 12H), 1.62 (s, 3H), 1.57 (br s, 2H), 1.54 (s, 3H), 1.04-1.51 (m, 9H), 0.98 (s, 3H), 0.98 (s, 3H), 0.89 (s, 3H), 0.85 (d, J=6.27 Hz, 3H), 0.82 (s, 3H), 0.63 (s, 3H).

Example 2: Study on the Hygroscopicity of the Crystal Form a of the Compound of Formula (I)

Experimental Materials:

SMS DVS Advantage Dynamic Vapor Sorption System

Experimental Method:

10 to 15 mg of the crystal form A of the compound of formula (I) was placed in the DVS sample tray for testing.

Figure 4:
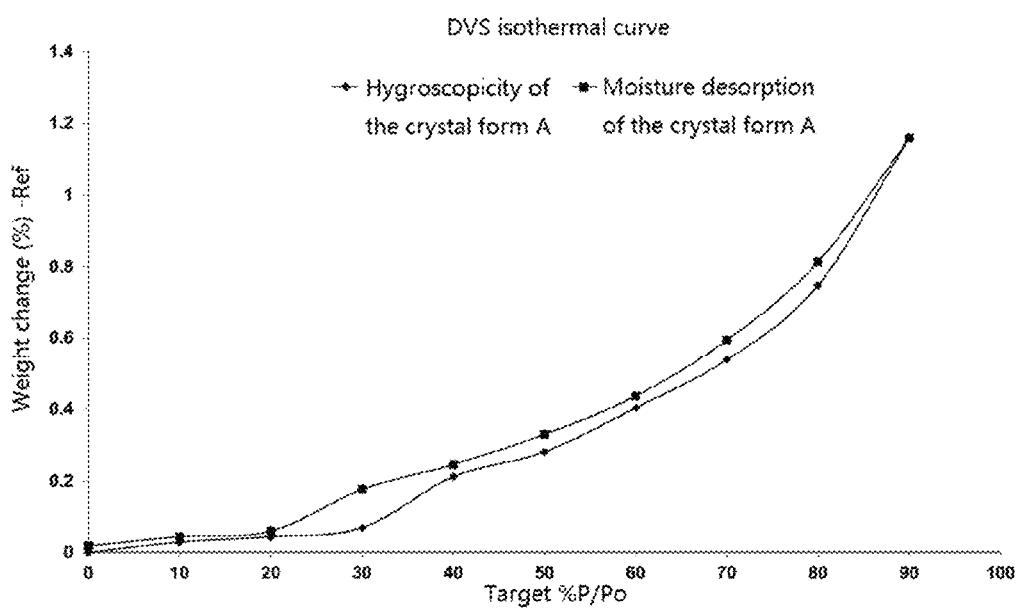
FIG. 4 is the DVS isotherm of the crystal form A.

Experimental Results:

The DVS pattern of the crystal form A of the compound of formula (I) is shown in FIG. 4, ΔW=0.747%.

Experimental Conclusion:

The hygroscopical weight gain of the crystal form A of the compound of formula (I) at 25° C. and 80% RH is 0.747%, which is slightly hygroscopic.

Example 3: Pre-Stability Experiment of the Crystal Form a of the Compound of Formula (I)

The crystal form A of the compound of formula (I) was placed under the following 3 conditions and tested for appearance, XRPD, content and related substances at different time points. The research conditions and testing items are shown in Table 2.

TABLE 2

Research conditions and test items

| Test item | Condition | Day 0 | Day 5 | Day 10 |
|---|---|---|---|---|
| Influencing factors | High temperature (60° C., open) | X* | X | X |
| | High humidity (relative humidity 92.5%, open) | | X | X |
| | Light (total illuminance = 1.2 × 10$^6$ Lux · hr/near ultraviolet = 200 w · hr/m$^2$, open) | | | X (1 ICH) |

Note:
*Testing item X includes: appearance, XRPD, content and related substances. The experiment was continued for 10 days;
ICH indicates the stability guideline on light stability testing.

Experimental Steps:

10 mg of the crystal form A of the compound of formula (I) was accurately weighted and placed in a sample bottle, and then spread to form a thin layer. The samples were placed under 60° C., 92.5% RH, the mouth of the bottle was directly wrapped with aluminum foil which was punctured to get some small holes to ensure that the sample can fully contact the ambient air. The samples were placed respectively in a dry box and a glass jar containing saturated potassium nitrate solution. The illuminated sample (open, not covered with aluminum foil) and the illuminated control sample (open, the sample bottle was entirely covered with aluminum foil) were placed in the light box. 2 parts of the sample were weighted at each time point as the formal test sample. In addition, about 5 mg of the crystal form A of the compound of formula (I) was weighted for XRPD testing; the sample bottle was wrapped with aluminum foil which was punctured to get some small holes; the samples were also placed in the corresponding drying box and the glass jar containing saturated potassium nitrate solution.

Content Analysis Method:

Column model: Ultimate XB-C18 3.0*50 mm, 3 μm; mobile phase: 0.5 mL TFA in 1 L water (solvent A) and 0.4 mL TFA in 1 L acetonitrile (solvent B), elution: an elution gradient of 95% to 100% (solvent B) for more than 2 minutes and then 100% for 13 minutes. The flow rate was 1.5 mL/min; column temperature: 30° C.

Experimental results and conclusions: the crystal form has not changed after the experiment, and its stability is good.

Biological Activity Test

Experimental Example 1: Study on the Penetration of Ocular Drugs in the Body and the Conversion of Drugs to Lanosterol In this study, New Zealand white rabbits (body weight was more than 2 kg, aged more than 12 weeks) were used as experimental animals. Each compound was studied in two New Zealand white rabbits. Each rabbit was instilled with 50 μL of eye drops in each eye, three eyes were used to collect aqueous humor samples and one eye was used as a backup. The formula of the eye drops was 1.2% hydroxypropyl methylcellulose (E5 size), 20.5% poloxamer (P407 size), 1.6% poloxamer (P188 size), the concentration of the compound was 5 mM, and the eye drops were homogeneous suspensions. After the eye drops were dripped into the rabbit's eyes, the anterior aqueous humor was collected 0.5, 2, 4 and 6 hours after administration. The volume of each sample was not more than 50 μL. Each animal was given mild anesthesia before collecting samples. Three samples were collected at each time point. The collected aqueous humor samples were stored in dry ice immediately after collection or stored in a refrigerator at −80±10° C. After the sample collection, the animals were euthanized. The concentration of the compound in each sample was determined using a triple quadrupole mass spectrometer (API 4000). Tables 3 and 4 show the DMPK determination conditions in vivo; Tables 5 and 6 show the drug concentration in the aqueous humor after compound lanosterol (parent drug) and the prodrug compound were dripped into eyes (250 nM per eye).

Experimental results and conclusions: both lanosterol itself and its prodrug compound of the present disclosure are capable of penetrating into the aqueous humor from the cornea or through other routes; and the prodrug compound is capable of converting into the parent drug lanosterol during the infiltration process and exhibits a higher concentration and exposure of lanosterol in the aqueous humor.

TABLE 3

In vivo DMPK analysis and determination methods

| Compound name | The compound of formula (I) and lanosterol |
| --- | --- |
| | Liquid chromatography method |
| Mobile phase A | A solution of water and acetonitrile (the volume ratio is 95:5) containing 0.025% formic acid, 1 mmol ammonium acetate buffer salt |
| Mobile phase B | A solution of acetonitrile and water (the volume ratio 95:5) containing 0.025% formic acid, 1 mmol ammonium acetate buffer salt |
| Chromatographic column | ACQUITY UPLC ® protein BEH 300A C4 1.7 μm 2.1 × 50 mm |
| Gradient | Flow rate (μL/min)   A (%)   B (%) |
| | 500 to 600   2 to 80   98 to 20 |

Mass spectrometry method

| Ion source | APCI or ESI |
| --- | --- |
| Scan mode | Multipolar ion monitoring |
| Polarity | Positive ions |

| Compound name | Ion pair | Retention time (min) | Declustering potential (eV) | Collision energy (eV) |
| --- | --- | --- | --- | --- |
| The compound of formula (I) | 409.3/109.1 | 2.05 | 50 | 38 |
| Lanosterol | 409.4/149.1 | 1.48 | 50 | 38 |

TABLE 4

The gradient of liquid chromatography method for DMPK testing of lanosterol and the compound of formula (I) in vivo

| | Gradient | | |
| --- | --- | --- | --- |
| Flow rate | Time (minute) | A (%) | B (%) |
| 500 μL/min | start | 80.0 | 20.0 |
| | 0.30 | 70.0 | 30.0 |
| | 1.20 | 20.0 | 80.0 |
| | 2.00 | 2.0 | 98.0 |
| | 2.30 | 2.0 | 98.0 |
| | 2.31 | 80.0 | 20.0 |
| | 2.40 | 80.0 | 20.0 |

TABLE 5

The average concentration of the sample in the aqueous humor (nM) after 250 nmol lanosterol was dripped into each eye of New Zealand white rabbit

| Eye drops compound name | Lanosterol (parent drug) |
| --- | --- |
| Test compound name | Lanosterol (parent drug) |
| Time (hour) | Average concentration (nM) |
| 0.5 | 106* |
| 2 | 496 |
| 4 | 300 |
| 6 | 225 |
| AUC (nM.h) | 1779 |

*BQL: below quantitation limit, AUC: exposure amount.

TABLE 6

The average concentration of the sample in the aqueous humor (nM) after 250 nmol the compound of formula (I) was dripped into each eye of New Zealand white rabbit

| Eye drops compound name | The compound of formula (I) (prodrug) | |
|---|---|---|
| Test compound name Time (hour) | The compound of formula (I) Average concentration (nM) | Lanosterol Average concentration (nM) |
| 0.5 | 41.0 | 471 |
| 2 | 33.3 | 478 |
| 4 | 25.5 | 403 |
| 6 | BQL | 586 |
| AUC (nM.h) | 124 | 2700 |

*BQL: below quantitation limit, AUC: exposure amount.

Experimental Example 2: Pharmacodynamic Study of Lanosterol Eye Drops and its Prodrug on Sodium Selenite-Induced Cataract Model in Neonatal New Zealand Rabbit 1. Experimental Animal P7 days old neonatal New Zealand rabbits, normal grade, and 5 young rabbits per litter were breast-fed with a mother rabbit.

2. Grouping and Processing

The experimental young rabbits were randomly divided into 5 groups with 5 rabbits per group.

1) Normal control group (NC): in the P10 day, the young rabbits were injected subcutaneously with 0.25 mL of physiological saline from the neck, and were not administered after the P15 day.

2) Model control group (MC): in the P10 day, the young rabbits were injected subcutaneously with sodium selenite solution (in physiological saline) at a dose of 20 μmol/kg body weight, and after the P15 day, drug-free blank eyes drops were dripped into the right eye 3 times every day for 42 days.

3) Positive control group (PC): in the P10 day, the young rabbits were injected subcutaneously with sodium selenite solution (in physiological saline) at a dose of 20 μmol/kg body weight, and after the P15 day, Kary Uni eye drops (Santen Pharmaceutical Co., Ltd in Japan) were dripped into the right eye 3 times every day for 42 days.

4) Lanosterol eye drops treatment group (LT): in the P10 day, the young rabbits were injected subcutaneously with sodium selenite solution (in physiological saline) at a dose of 20 μmol/kg body weight, and after the P15 day, lanosterol eye drops were dripped into the right eye 3 times every day for 42 days.

5) Lanosterol prodrug 026 eye drops treatment group (026, the compound of formula (I)): in the P10 day, the young rabbits were injected subcutaneously with sodium selenite solution (in physiological saline) at a dose of 20 μmol/kg body weight, and after the P15 day, lanosterol prodrug 026 eye drops were dripped into the right eye 3 times every day for 42 days.

3. Experimental Test

1) Slit lamp photography: sodium selenite-induced neonatal New Zealand rabbits in each group were observed with slit lamp before the administration, and 7 days, 14 days, 21 days and 42 days after the administration respectively;

2) Lens transparency testing in vitro: on the last day, the animal's eyeball was dissected, the lens containing the capsule was completely separated, and the lens was placed on a grid paper (2.12×2.12 mm). The photographs show the sharpness of the grid photographed through the lens.

3) Glutathione peroxidase (GSH-PX) activity assay: GSH-PX activity of the isolated rabbit lens in each group was determined by the method provided in the specification of GSH-PX activity detection kit (Nanjing Jiancheng Bioengineering Institute). The experimental data was analyzed by One-Way ANOVA with SPSS statistical software. The LSD method was used to compare the groups, and the statistical difference level was $p<0.05$.

4. Experimental Results

Figure 5:
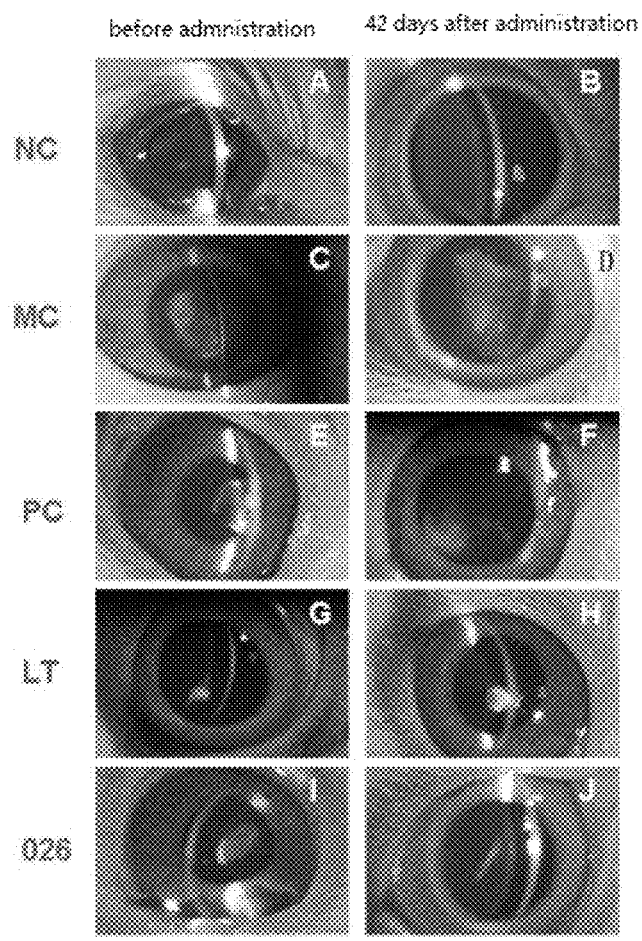
FIG. 5 is the effect of lanosterol and its prodrug 026 eye (the compound of formula (I)) drops on sodium selenite-induced neonatal New Zealand rabbit cataract model observed by slit lamp. NC: normal control group; MC: model control group; PC: positive control group; LT: lanosterol eye drops treatment group; 026: lanosterol prodrug 026 eye drops treatment group.

1) Slit lamp observation: FIG. 5 shows that sodium selenite could induce cataract in neonatal New Zealand rabbit lens. Slit lamp observation shows the cataract symptoms were significantly reduced after lanosterol prodrug 026 eye drops were administered for 42 days (FIG. 5-I) compared with the symptoms before administration (FIG. 5-J). The cataract symptoms showed no evident change before and after the administration of Kary Uni eye drops (FIGS. 5-E, 5-F) and lanosterol eye drops (FIG. 5-G, 5-H).

Figure 6:
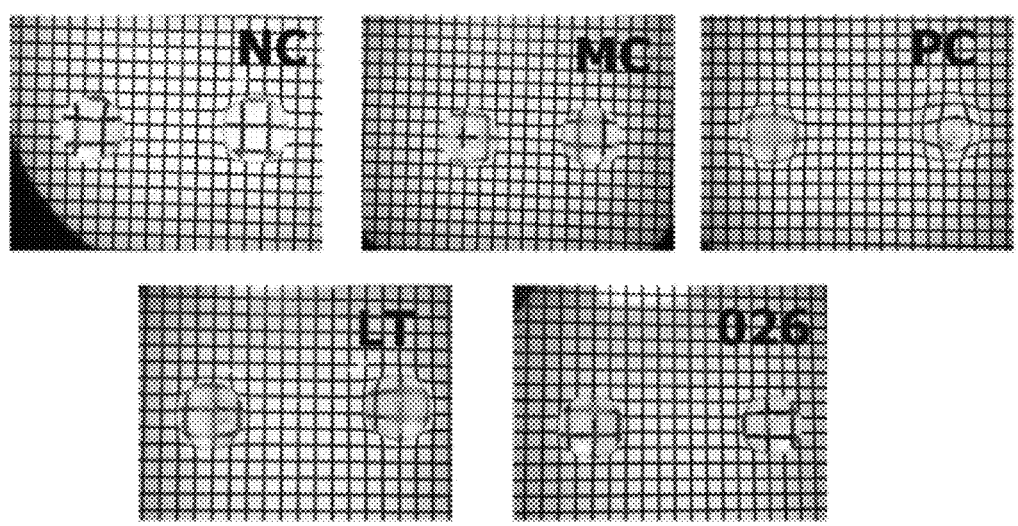
FIG. 6 is the comparison of lens transparency of sodium selenite-induced neonatal New Zealand rabbit cataract model in each group in vitro after 42 days of administration. NC: normal control group; MC: model control group; PC: positive control group; LT: lanosterol eye drops treatment group; 026: lanosterol prodrug 026 eye drops treatment group. Grid is 2.12×2.12 mm.

2) Lens transparency test in vitro: FIG. 6 shows the lens transparency of neonatal New Zealand rabbits with sodium selenite-induced cataract in each group after 42 days of administration. On the left side of each photograph is the left eye lens (left eye was not administered as a self-control), and on the right is the right eye lens (the right eye was administered according to grouping). After 42 days of administration of lanosterol prodrug 026 eye drops, the transparency of the right eye lens was significantly higher than that of the left eye, and also significantly higher than that of the MC group, but it was still lower than that of the NC group. There was no significant change in lens transparency after administration to the right eye in the LT group.

Figure 7:
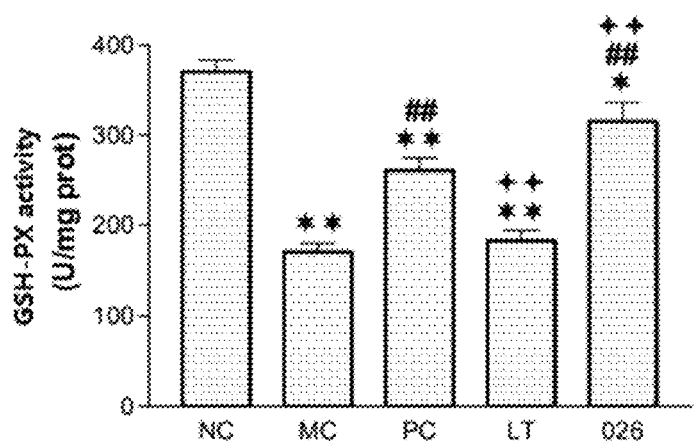
FIG. 7 is the comparison of lens glutathione peroxidase (GSH-PX) activity of sodium selenite-induced neonatal New Zealand rabbit cataract model after 42 days of administration. NC: normal control group; MC: model control group; PC: positive control group; LT: lanosterol eye drops treatment group; 026: lanosterol prodrug 026 eye drops treatment group. VS NC: ** means p<0.01, * means p<0.05; VS MC: ## means p<0.01, # means p<0.05; VS PC: ++ means p<0.01, + means p<0.05.

3) GSH-PX activity assay: after 42 days of administration, the result of the GSH-PX activity of the lens in each group shows (see FIG. 7) that after subcutaneous injection of sodium selenite, the activity of GSH-PX in the lens of rabbit eyes was significantly reduced and there was a statistical difference ($p<0.01$) compared to the NC group. The lanosterol prodrug 026 eye drops and the positive control drug Kary Uni eye drops were capable of increasing the GSH-PX activity of the lens, and there was a statistical difference compared to the MC group ($p<0.01$), and the improvement effect of 026 was better than that of Kary Uni ($p<0.01$). The effect of lanosterol eye drops on the activity of lens GSH-PX was significantly lower than that of 026 and Kary Uni, and there was no statistical difference compared to the MC group ($p>0.05$).

5. Conclusion

The above results indicate that the lanosterol prodrug 026 eye drops are capable of alleviating the cataract symptoms of neonatal New Zealand rabbits induced by sodium selenite and improving lens transparency and lens GSH-PX activity.

Experimental Example 3: Pharmacodynamic Study of Lanosterol Eye Drops and its Prodrug on Ultraviolet-Induced Neonatal New Zealand Rabbit Cataract Model 1. Experimental Animal Adult New Zealand rabbits 2.0-2.5 kg, normal grade, male and female, a total of 25.

Grouping and Processing

The experimental rabbits were randomly divided into 5 groups with 5 rabbits per group.

1) Normal control group (NC): normal feeding, no drug administration.

2) Model control group (MC): 313 nm UV irradiation for 24 hours to make model, then drug-free blank eye drops were dripped into the right eye 3 times every day for 42 days.

3) Positive control group (PC): 313 nm UV irradiation for 24 hours to make model, then Kary Uni eye drops (Santen Pharmaceutical Co., Ltd in Japan) were dripped into the right eye 3 times every day for 42 days.

4) Lanosterol eye drops treatment group (LT): 313 nm UV irradiation for 24 hours to make model, then lanosterol eye drops were dripped into the right eye 3 times every day for 42 days.

5) Lanosterol prodrug 026 eye drops treatment group (026): 313 nm UV irradiation for 24 hours to make model, then the lanosterol prodrug 026 eye drops were dripped into the right eye 3 times every day for 42 days.

3. Experimental Test

1) Slit lamp photography: The animals in each group were observed with slit lamp before the administration, and 7 days, 14 days, 21 days and 42 days after the administration respectively;

2) Lens transparency test in vitro: on the last day, the animal's eyeball was dissected, the lens containing the capsule was completely separated, and the lens was placed on a grid paper (2.12×2.12 mm). The photographs show the sharpness of the grid photographed through the lens.

3) Glutathione peroxidase (GSH-PX) activity assay: GSH-PX activity of the isolated rabbit lens in each group was determined by the method provided in the specification of GSH-PX activity detection kit (Nanjing Jiancheng Bio-engineering Institute). The experimental data were analyzed by One-Way ANOVA with SPSS statistical software. The LSD method was used to compare the groups, and the statistical difference level was $p<0.05$.

4. Experimental Results

Figure 8:
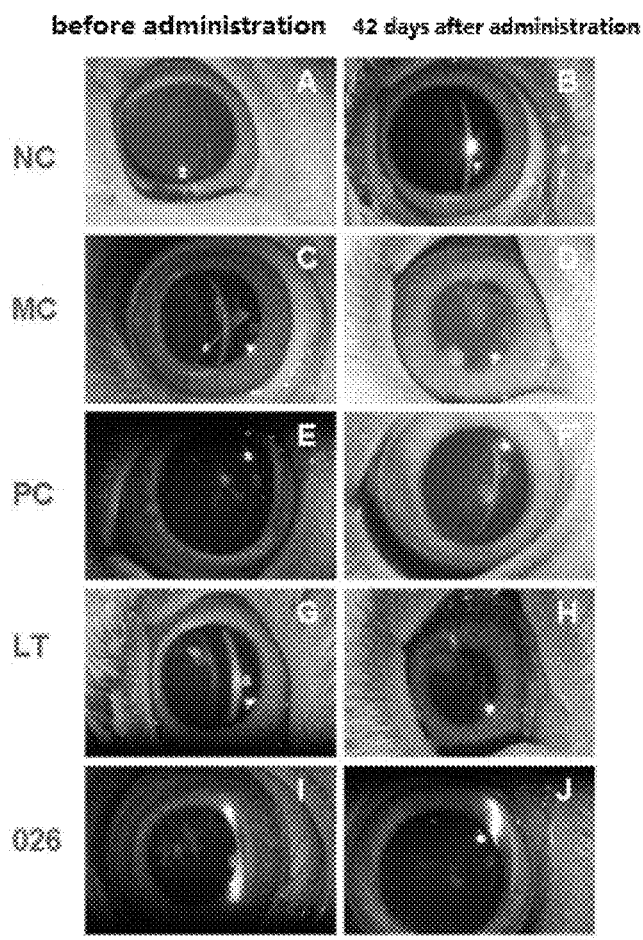
FIG. 8 is the effect of lanosterol and its prodrug 026 eye drops on ultraviolet-induced New Zealand rabbit cataract model observed by slit lamp. NC: normal control group; MC: model control group; PC: positive control group; LT: lanosterol eye drops treatment group; 026: lanosterol prodrug 026 eye drops treatment group.

1) Slit lamp observation: FIG. 8 shows that ultraviolet induced cataract in New Zealand rabbit lens. Slit lamp observation shows the cataract symptoms were significantly reduced after lanosterol prodrug 026 eye drops were administered for 42 days (FIG. 8-I) compared with the symptoms before administration (FIG. 8-J). The cataract symptoms showed no evident change before and after the administration of Kary Uni eye drops (FIGS. 8-E, 8-F) and lanosterol eye drops (FIG. 8-G, 8-H).

Figure 9:
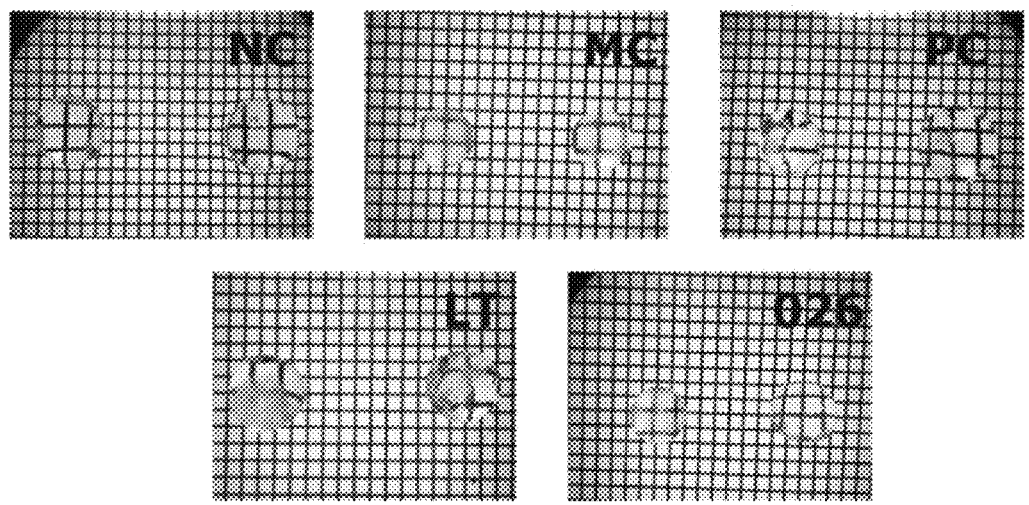
FIG. 9 is the comparison of lens transparency of ultraviolet-induced New Zealand rabbit cataract in each group in vitro after 42 days of administration. NC: normal control group; MC: model control group; PC: positive control group; LT: lanosterol eye drops treatment group; 026: Lanosterol prodrug 026 eye drops treatment group. Grid is 2.12×2.12 mm.

2) Lens transparency test in vitro: FIG. 9 shows the lens transparency of New Zealand rabbits with cataract induced by ultraviolet in each group after 42 days of administration. On the left side of each photograph is the left eye lens (left eye was not administered as a self-control), and on the right is the right eye lens (the right eye was administered according to grouping). After 42 days of administration of lanosterol prodrug 026 eye drops, the transparency of the right eye lens was significantly higher than that of the left eye, and also significantly higher than that of the MC group, but it was still lower than that of the NC group. There was no significant change in lens transparency after drug administration to the right eye in the LT group.

Figure 10:
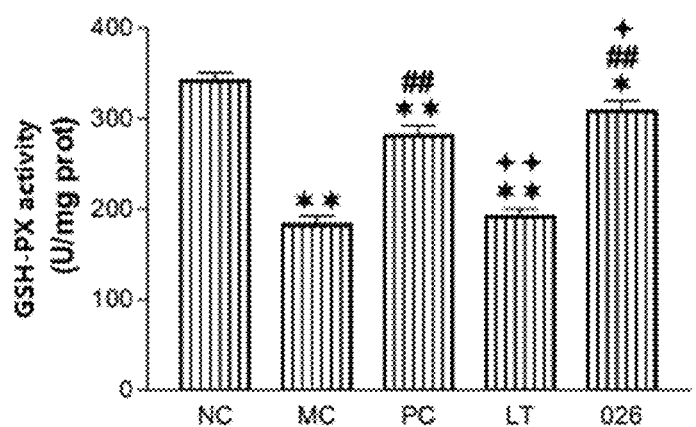
FIG. 10 is the comparison of lens glutathione peroxidase (GSH-PX) activity of ultraviolet-induced neonatal New Zealand rabbit cataract in each group after 42 days of administration. NC: normal control group; MC: model control group; PC: positive control group; LT: lanosterol eye drops treatment group; 026: lanosterol prodrug 026 eye drops treatment group. VS NC: ** means p<0.01, * means p<0.05; V.S MC: ## means p<0.01, # means p<0.05; VS PC: ++ means p<0.01, + means p<0.05.

3) GSH-PX activity assay: after 42 days of administration, the GSH-PX activity of the lens in each group shows (see FIG. 10) that after UV irradiation, the activity of GSH-PX in the lens of rabbit eyes was significantly reduced and there was a statistical difference compared to the NC group ($p<0.01$ or $p<0.05$). The lanosterol prodrug 026 eye drops and the positive control drug Kary Uni eye drops were capable of increasing the GSH-PX activity of the lens, and there was a statistical difference compared to the MC group ($p<0.01$), and the improvement effect of 026 is better than that of Kary Uni ($p<0.05$). The effect of lanosterol eye drops on the activity of lens GSH-PX was significantly lower than that of 026 and Kary Uni, and there was no statistical difference compared to the MC group ($p>0.05$).

5. Conclusion

The above results indicate that the lanosterol prodrug 026 eye drops are capable of alleviating the cataract symptoms of New Zealand rabbits induced by UV irradiation, and improving lens transparency and lens GSH-PX activity.

What is claimed is:

1. A crystal form A of the compound of formula (I), wherein the X-ray powder diffraction pattern (XPRD) of the crystal form A comprises characteristic diffraction peaks at the following angles of 2θ: 8.60±0.2°, 15.06±0.2° and 17.22±0.2°;

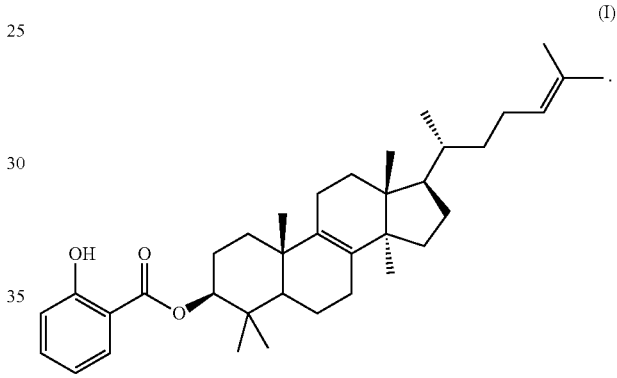

2. The crystal form A as defined in claim 1, wherein the X-ray powder diffraction pattern of the crystal form A comprises characteristic diffraction peaks at the following angles of 2θ: 8.60±0.2°, 9.38±0.2°, 10.57±0.2°, 12.54±0.2°, 14.43±0.2°, 15.06±0.2°, 17.22±0.2° and 25.18±0.2°.

3. The crystal form A as defined in claim 2, wherein the X-ray powder diffraction pattern of the crystal form A comprises characteristic diffraction peaks at the following angles of 2θ: 4.350°, 8.598°, 9.383°, 10.566°, 12.542°, 13.448°, 14.428°, 14.591°, 15.063°, 15.453°, 15.820°, 16.803°, 17.216°, 20.985°, 21.181°, 22.225°, 22.601°, 22.856°, 23.726°, 24.039°, 24.534°, 25.185°, 25.514°, 25.935°, 26.570°, 27.867°, 28.125°, 28.416°, 29.114°, 29.445°, 31.914°, 33.710°, 34.297°, 34.329°, 36.014°, 36.108° and 38.196°.

Figure 1:
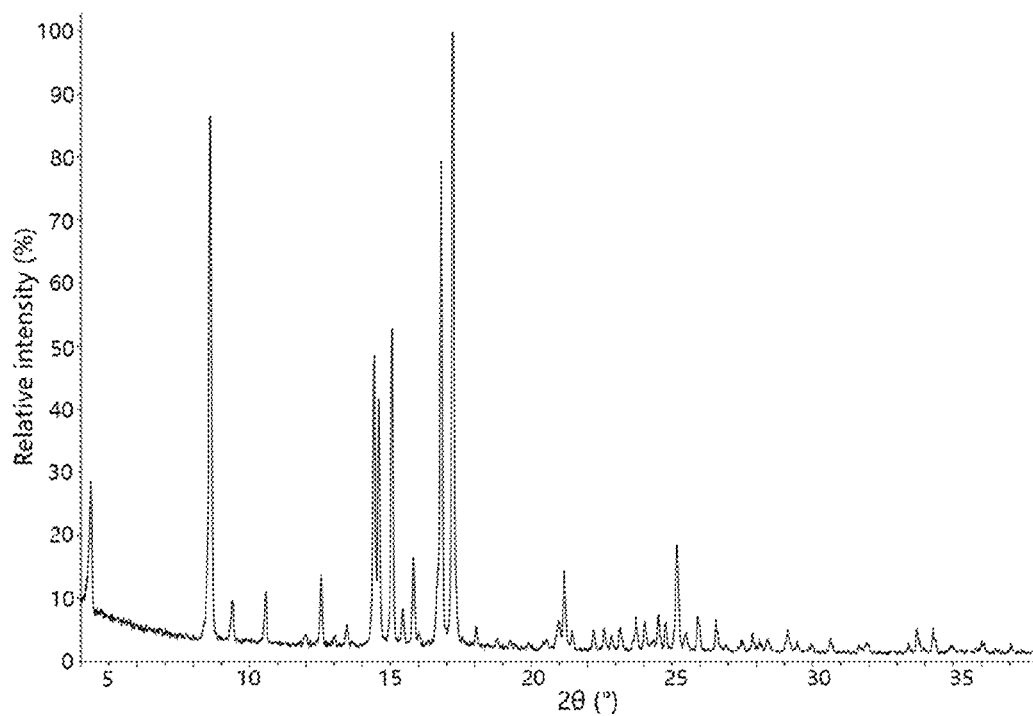
FIG. 1 is the XRPD pattern of the crystal form A radiated by Cu-Kα.

4. The crystal form A as defined in claim 3, wherein the X-ray powder diffraction pattern of the crystal form A is as shown in FIG. 1.

5. The crystal form A as defined in claim 1, wherein the differential scanning calorimetry (DSC) pattern of the crystal form A has an endothermic peak with onset at 151.75±3° C.

Figure 2:
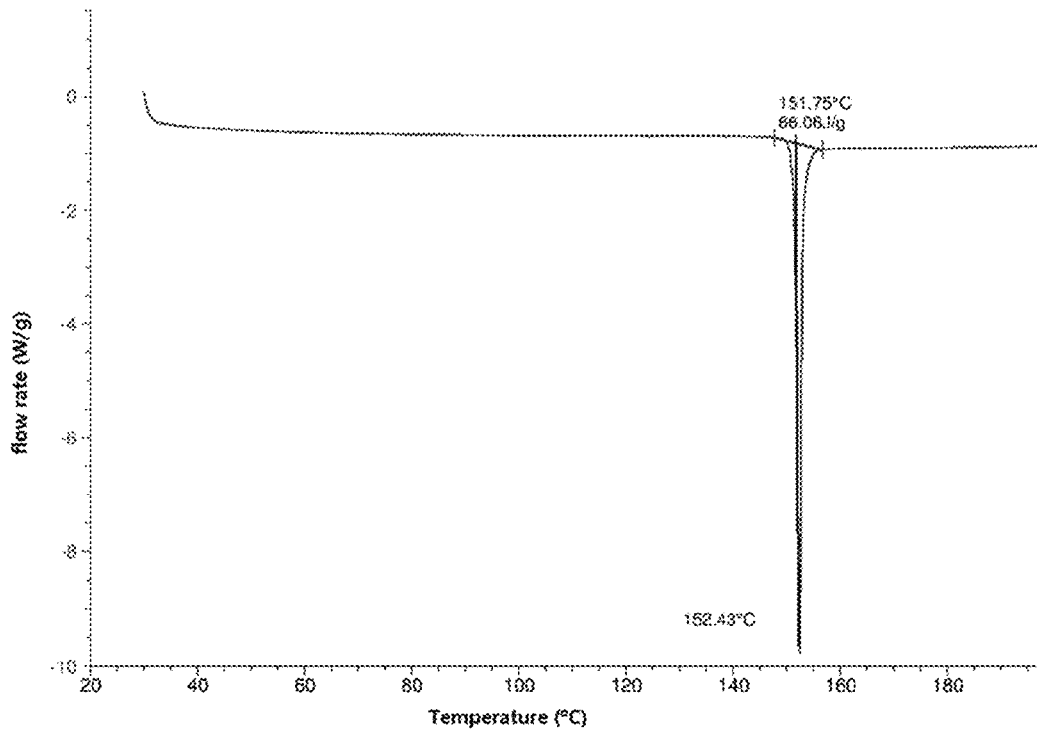
FIG. 2 is the DSC pattern of the crystal form A.

6. The crystal form A as defined in claim 5, wherein the DSC pattern of the crystal form A is as shown in FIG. 2.

7. The crystal form A as defined in claim 1, wherein the thermogravimetric analysis (TGA) pattern of the crystal form A has a weight loss of 0.04540% occurred at 151.57±3° C.

Figure 3:
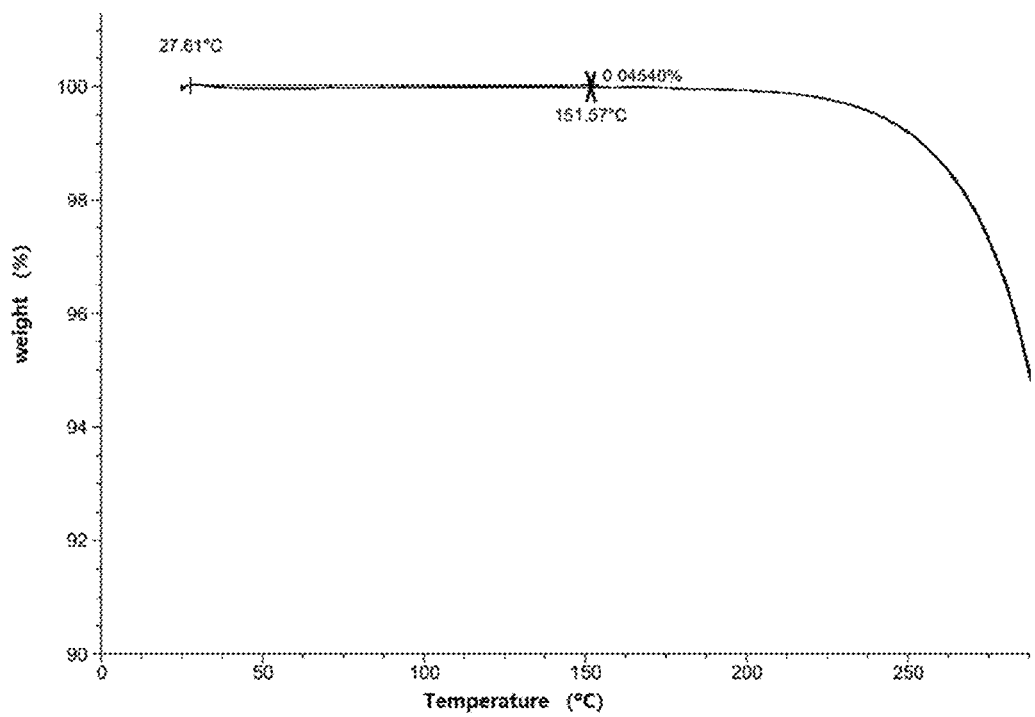
FIG. 3 is the TGA pattern of the crystal form A.

8. The crystal form A as defined in claim 7, wherein the TGA pattern of the crystal form A is as shown in FIG. 3.

* * * * *